(12) United States Patent
Matsumura et al.

(10) Patent No.: US 6,624,320 B2
(45) Date of Patent: Sep. 23, 2003

(54) ASYMMETRIC PHOSPHINE LIGAND

(75) Inventors: Kazuhiko Matsumura, Hiratsuka (JP); Takao Saito, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/291,364

(22) Filed: Nov. 12, 2002

(65) Prior Publication Data
US 2003/0144138 A1 Jul. 31, 2003

(30) Foreign Application Priority Data
Dec. 10, 2001 (JP) ........................................ 2001-375218

(51) Int. Cl.$^7$ ................................ C07F 9/00; C07F 9/50
(52) U.S. Cl. .............................. 556/21; 568/12; 568/17
(58) Field of Search ............................... 568/8, 12, 17, 568/13; 556/13, 20, 21

(56) References Cited

U.S. PATENT DOCUMENTS

| | | | | |
|---|---|---|---|---|
| 5,008,457 A | | 4/1991 | Burk | 568/12 |
| 5,171,892 A | | 12/1992 | Burk | 568/12 |
| 5,206,398 A | * | 4/1993 | Burk | 556/16 |
| 5,386,061 A | * | 1/1995 | Burk | 568/12 |
| 5,801,263 A | * | 9/1998 | Seitz et al. | 558/155 |
| 5,874,600 A | * | 2/1999 | Rautenstrauch et al. | 556/136 |
| 6,043,396 A | * | 3/2000 | Sturmer et al. | 568/12 |
| 6,207,868 B1 | | 3/2001 | Zhang | 568/814 |
| 6,278,024 B1 | | 8/2001 | Zhang | 568/17 |
| ,047,113 A1 | | 11/2001 | Zhang | |
| 6,380,416 B2 | | 4/2002 | Zhang | 558/156 |
| 6,399,787 B1 | | 6/2002 | Zhang | 548/469 |

FOREIGN PATENT DOCUMENTS

| | | |
|---|---|---|
| WO | 99/59721 | 11/1999 |
| WO | 00/11008 | 3/2000 |
| WO | 00/26220 | 5/2000 |

OTHER PUBLICATIONS

CA:109:149617 abs of Journal of Organometallic Chemistry by Issleib et al 330(1–2) pp 17–24 1987.*
CA:128:48304 abs of Synthesis by Brunner et al (11) pp 1309–1314 1997.*
CA:135:227050 abs of Tetrahedron: Asymmetry 12(8) pp 1159–1169 2001.*
Kottsieper, et al., "Synthesis of enantiopure $C_1$ symmetric diphosphines and . . . ", Tetrahedron, vol. 12 (2001), pp. 1159–1169.
Holz, et al., "Synthesis of a New Class of Functionalized Chiral . . . ", J. Org. Chem., vol. 63 (1998), pp. 8031–8034.
Brunner, et al., "Asymmetric Catalyses", Journal of Organometallic Chemistry, vol. 328 (1987), pp. 71–80.
Reetz, et al., "New Non–$C_2$–symmetric phosphine–phosphonites as ligands . . . ", Tetrahedron: Asymmetry 10 (1999), pp. 2129–2137.

* cited by examiner

Primary Examiner—Jean F. Vollano
(74) Attorney, Agent, or Firm—Fitzpatrick, Cella, Harper & Scinto

(57) ABSTRACT

A novel phosphine compound having excellent properties (chemical selectivity, enantioselectivity, catalytic activity) as a catalyst for asymmetric syntheses, especially asymmetric hydrogenation. A phosphine-phosphorane compound represented by the following general formula:

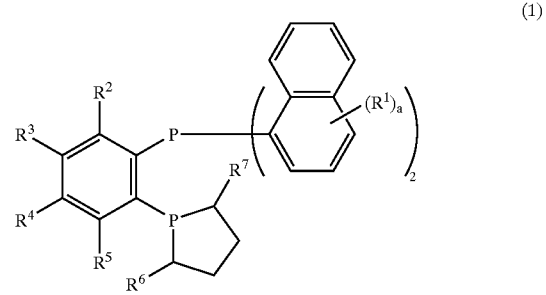

(1)

(wherein $R^1$ represents hydrogen atom or a linear or branched alkyl group having 1 to 4 carbon atoms, $R^2$, $R^3$, $R^4$, and $R^5$ are the same or different, and each represents hydrogen atom, or an alkyl group having 1 to 6 carbon atoms, etc., and each of $R^2$ and $R^3$, $R^3$ and $R^4$, and $R^4$ and $R^5$ may be together combined to form a ring which may contain one or more (preferably 1 to 2) oxygen atoms, and $R^6$ and $R^7$ are the same or different, and each represents a linear or branched alkyl group having 1 to 6 carbon atoms, etc.).

7 Claims, No Drawings

ASYMMETRIC PHOSPHINE LIGAND

FIELD OF THE INVENTION

The present invention relates to a novel phosphine-phosphorane compound, a production intermediate thereof, a transition metal complex containing the phosphine-phosphorane compound as a ligand, and a catalyst useful as a catalyst for various asymmetric syntheses, and a catalytic asymmetric synthetic technology using the same. Furthermore, the invention relates to a novel optically active phosphine-phosphorane compound, a production intermediate thereof, a transition metal complex containing the optically active phosphine-phosphorane compound as a ligand, and a catalyst useful as a catalyst for various asymmetric syntheses, and a catalytic asymmetric synthetic technology using the same.

BACKGROUND OF THE INVENTION

Hitherto, many reports have been made on the transition metal complex catalysts capable of being utilized in catalytic asymmetric syntheses such as asymmetric hydrogenation, asymmetric transfer hydrogenation, asymmetric hydrosilylation, asymmetric hydroboration, asymmetric hydroformylation, asymmetric isomerization of olefins, and asymmetric Heck reaction. Particularly, it is reported that complexes of transition metals such as ruthenium, iridium, rhodium, palladium, and nickel containing various optically active phosphines as ligands exhibit excellent performance as catalysts for asymmetric syntheses, and some of the catalysts are industrially employed (Asymmetric Catalysis in Organic Synthesis, Ed., R Noyori, Wiley & Sons, New York (1994)). Among the ligands, phosphorane-type ligands are disclosed and transition metal complexes containing the ligands are reported to be useful as the catalysts for catalytic asymmetric syntheses such as asymmetric hydrogenation ((1) H. Burunner, R. Sievi, J. Organometal. Chem., 1987, 328, 71; (2) WO 91/17998 (BPE); (3) WO 93/01199 (DuPHOS); (4) J. Org. Chem., 1998, 63, 8031 (RoPHOS); (5) WO 00/11008; (6) WO 99/59721 (PennPhos); (7) WO 00/26220; and so forth).

However, all the phosphorane-type ligands shown in (1) to (6) contain two optically active phosphorane rings per one molecule, so that their preparation requires a large amount of expensive optically active 1,3- or 1,4-diols. Moreover, in the synthesis of the diphosphine shown in (7), it is necessary to introduce an optically active center onto a phosphorus atom, which is difficult to synthesize. Thus, there is an inconvenience that these ligands are not suitable for practical use.

SUMMARY OF THE INVENTION

Thus, it is an object of the invention to provide a novel phosphine compound which can be synthesized from a small amount of an optically active compound and has excellent properties (chemical selectivity, enantioselectivity, catalytic activity) as a catalyst for asymmetric syntheses, especially asymmetric hydrogenation.

As a result of intensive studies for solving the above problem, the present inventors have found that a transition metal complex of an optically active phosphine-phosphorane having a specific structure is effective for asymmetric hydrogenation.

Moreover, they have found that the transition metal complex exhibits excellent catalytic activity and enantio- or diastereo-selectivity in asymmetric hydrogenation of olefins such as enamides and β-monosubstituted dehydroamino acid derivatives, and accomplished the invention.

Incidentally, a ligand containing one optically active phosphorane ring per one molecule has been reported in "Tetrahedron; Asymmetry 2001, 12, 1159", which discloses the compound and process for producing the same but does not describe the preparation of an complex from a transition metal and the compound and the process of asymmetric hydrogenation of a substrate in the presence of the complex, still less the compound having a substituent other than phenyl group on the phosphine and the process for producing the same.

DETAILED DESCRIPTION OF THE INVENTION

The following will explain the invention in detail.

The phosphine-phosphorane compound of the invention is represented by the general formula (1).

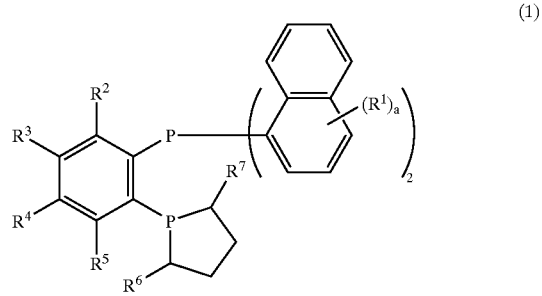

(1)

(wherein $R^1$ represents hydrogen atom, a linear or branched alkyl group having 1 to 4 carbon atoms, or an alkoxy group having 1 to 6 carbon atoms and a represents an integer of 1 to 4; $R^2$, $R^3$, $R^4$, and $R^5$ are the same or different, and each represents hydrogen atom, an alkyl group having 1 to 6 carbon atoms, or an alkoxy group having 1 to 6 carbon atoms, and each of $R^2$ and $R^3$, $R^3$ and $R^4$, and $R^4$ and R5 may be together combined to form a ring which may contain one or more (preferably 1 to 2) oxygen atoms; and $R^6$ and $R^7$ are the same or different, and each represents a linear or branched alkyl group having 1 to 6 carbon atoms, a cycloalkyl group having 3 to 7 carbon atoms, a perfluoroalkyl group, a phenyl group, a phenyl group having one or more (preferably 1 to 5) substituents (an alkyl group having 1 to 6 carbon atoms, an alkyl group having 1 to 6 carbon atoms which is substituted by one or more (preferably 1 to 7) halogen atoms, an alkoxy group having 1 to 6 carbon atoms, or a halogen atom), an aralkyl group having 7 to 12 carbon atoms, or a ring-substituted aralkyl group).

The alkyl group having 1 to 4 carbon atoms for the above $R^1$ is selected from the group consisting of methyl group, ethyl group, n-propyl group, iso-propyl group, n-butyl group, iso-butyl group, sec-butyl group, and tert-butyl group, and the alkoxy group having 1 to 6 carbon atoms includes methoxy group, ethoxy group, n-propyloxy group, iso-propyloxy group, n-butoxy group, iso-butoxy group, sec-butoxy group, tert-butoxy group, n-pentyloxy group, iso-pentyloxy group, neo-pentyloxy group, tert-pentyloxy group, 2-methylpentyloxy group, n-hexyloxy group, and iso-hexyloxy group.

The alkyl group having 1 to 6 carbon atoms for $R^2$, $R^3$, $R^4$, or $R^5$ is selected from the group consisting of methyl group, ethyl group, n-propyl group, iso-propyl group, n-butyl group, iso-butyl group, sec-butyl group, tert-butyl group, n-pentyl group, iso-pentyl group, neo-pentyl group, tert-pentyl group, 2-methylpentyl group, n-hexyl group, and iso-hexyl group, and the alkoxy group having 1 to 6 carbon atoms includes methoxy group, ethoxy group, n-propyloxy group, iso-propyloxy group, n-butoxy group, iso-butoxy group, sec-butoxy group, tert-butoxy group, n-pentyloxy group, iso-pentyloxy group, neo-pentyloxy group, tert-pentyloxy group, 2-methylpentyloxy group, n-hexyloxy group, and iso-hexyloxy group.

Furthermore, each of $R^2$ and $R^3$, $R^3$ and $R^4$, and $R^4$ and $R^5$ may be together combined to form a ring, and the ring is preferably a ring having 5 to 7 carbon atoms, which is formed together with other carbon atoms. The ring may have one or more (preferably 1 to 5) substituents.

Specific examples thereof include rings containing methylenedioxy group, ethylenedioxy group, or propylenedioxy group, benzene, indane, tetrahydronaphthalene, indene, dihydronaphthalene, fluorene, naphthalene, anthracene, phenanthrene, and the like. The substituent for the rings includes an alkyl group having 1 to 6 carbon atoms, an alkoxy group having 1 to 6 atoms, an alkyl group having 1 to 6 carbon atoms substituted by one or more (preferable 1 to 7) halogen atoms, a halogen atom, amino group, an amino group substituted by one or more (preferable 1 to 2) alkyl groups, and the like. The alkyl group having 1 to 6 carbon atoms and the alkoxy group having 1 to 6 atoms are selected from those the same as the above.

The linear or branched alkyl group having 1 to 6 carbon atoms for the above $R^6$ or $R^7$ is selected from those the same as the above. The cycloalkyl group having 3 to 7 carbon atoms is preferably cyclopropyl group, methylcyclopropyl group, cyclobutyl group, cyclopentyl group, 2-methylcyclopentyl group, 3-methylcyclopentyl group, cyclohexyl group, 2-methylcyclohexyl group, 3-methylcyclohexyl group, 4-methylcyclohexyl group, or cycloheptyl group.

The phenyl group may have one or more (preferable 1 to 5) substituents and the alkyl group having 1 to 6 carbon atoms as the substituent is selected from those the same as above. The alkyl group by which the phenyl group is substituted may be further substituted by one or more (preferable 1 to 7) halogen atoms each selected from fluorine atom, chlorine atom, iodine atom, or the like. Moreover, the halogen atom by which the phenyl group is substituted is selected from fluorine atom, chlorine atom, iodine atom, or the like, and the alkoxy group having 1 to 6 atoms is selected from those the same as above.

The perfluoroalkyl group includes trifluoromethyl group and pentafluoroethyl group.

The aralkyl group having 7 to 12 carbon atoms is preferably benzyl group, 2-phenylethyl group, 1-phenylpropyl group, 2-phenylpropyl group, 3-phenylpropyl group, 1-phenylbutyl group, 2-phenylbutyl group, 3-phenylbutyl group, 4-phenylbutyl group, 1-phenylpentyl group, 2-phenylpentyl group, 3-phenylpentyl group, 4-phenylpentyl group, 5-phenylpentyl group, 1-phenylhexyl group, 2-phenylhexyl group, 3-phenylhexyl group, 4-phenylhexyl group, 5-phenylhexyl group, or 6-phenylhexyl group. Moreover, the substituent on the aralkyl group includes an alkyl group having 1 to 6 carbon atoms, an alkoxy group having 1 to 6 atoms, and a halogen atom, each of which is selected from those the same as above.

The phosphine-primary phosphine of the invention is represented by the general formula (2).

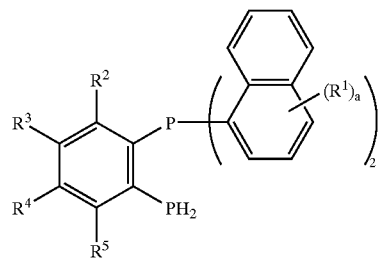

(2)

(wherein $R^1$ to $R^5$ and a are the same as above)

The compound represented by the general formula (2) is a production intermediate of the compound represented by the general formula (1).

The invention includes racemic compounds, meso-isomers, and optically active compounds of the above compounds.

The following will explain the production method of these compounds.

First, in order to avoid complication, the representative production method of the compound of the invention is specifically explained using the compound represented by the following formula (3): 1-((2S,5S)-2,5-dimethylphosphorano)-2-[di(1-naphthyl)phosphino]benzene (hereinafter, sometimes referred to as (S,S)-Me-UCAP-(1-Nap)) among the compounds included in the invention as an example. Of course, the invention is not limited to the examples.

The compound of the following formula (3) can be represented by the following formula.

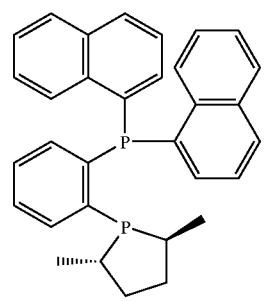

(3)

For example, 2-bromophenol (4) is reacted with trifluoromethanesulfonic anhydride to form 2-(trifluoromethanesulfonyl)oxy-bromobenzene (5), which is then reacted with di(1-naphthyl)phosphine in the presence of a palladium complex catalyst to obtain (2-bromophenyl)[di(1-naphthyl)]phosphine (6). Next, the compound (6) is reacted with diethyl chlorophosphite in the presence of n-butyllithium to obtain diethyl 2-[di(1-naphthyl)phosphino]phenylphosphonite (7). Then, the compound (7) is reduced with lithium aluminum hydride in the presence of chlorotrimethylsilane to form [2-[di(1-naphthyl)phosphino]phenylphosphine (8). Thereafter, in the presence of n-butyllithium, the compound is reacted with dimesylate of (2R,5R)-2,5-hexanediol producible, for example, according to the method described in a literature (Tetrahedron: Asymmetry, 1991, 2, 569), whereby the aimed (S,S)-Me-UCAP-(1-Nap) (3) can be produced in a high efficiency.

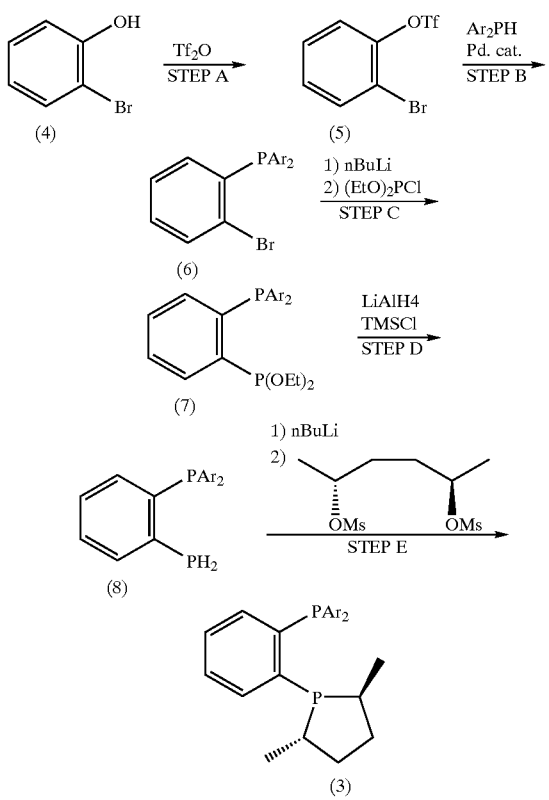

Ar = 1-naphthyl
Tf = CF₃SO₂

The reaction in Step A is a reaction wherein the hydroxyl group of a 2-hydroxyaryl halide (4) is triflated to form a 2-(trifluoromethanesulfonyl)oxy-aryl halide (5) and is carried out in accordance with the method of triflation of 1,1'-binaphthol described in a known literature (Tetrahedron Lett., 1990, 31, 6321). If necessary, the compound (5) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction in Step B is a reaction wherein a 2-(halophenyl)phosphine (6) is formed by reacting 2-(trifluoromethanesulfonyloxy)-aryl halide (5) with a phosphine compound in the presence of a catalyst of a transition metal such as palladium, the reaction being carried out in accordance with the method described in a known literature (Tetrahedron Lett., 1990, 31, 6321). If necessary, the compound (6) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of the first step of Step C is a reaction wherein the C-Br bond of the compound (6) is cleaved and metalated. The reagent for use in the metalation includes an alkali metal (e.g., lithium, sodium, or potassium), an alkaline earth metal (e.g., magnesium), or a derivative thereof (e.g., sodium-cyclopentadiene, sodium bistrimethylsilylamide, potassium hydride, potassium amide, or a Grignard reagent). Preferably, the C—Br bond can be cleaved and metalated by treating the compound with a reagent which is known as a lithiation reagent in the field of organic synthesis, such as methyllithium, n-butyllithium, sec-butyllithium, tert-butyllithium, phenyllithium, or lithium diisopropylamide.

The reaction is preferably carried out in the presence of a solvent and use can be made of a usual solvent which does not adversely influence the reaction. Preferred is an inert solvent including an ether such as diethyl ether, diisopropyl ether, tetrahydrofuran (THF), 1,4-dioxane, or 1,2-dimethoxyethane, or a hydrocarbon such as pentane, hexane, or methylcyclohexane. These solvents may be used solely or as a mixed solvent. These solvents are referred to below as "aforementioned solvents". If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The reaction temperature is from about −100° C. to about room temperature, and usually, the reaction is preferably carried out under a cooled condition, for example, under cooling with dry ice-acetone bath or dry ice-2-propanol bath.

Next, the reaction of the second step of Step C is a reaction wherein a phosphine derivative is formed by the reaction with a phosphorus-containing compound such as chlorophosphite. The phosphorus-containing compound includes dimethyl chlorophosphite, diethyl chlorophosphite, di(n-propyl) chlorophosphite, diisopropyl chlorophosphite, di(n-butyl) chlorophosphite, and diphenyl chlorophosphite. Preferably, a phosphine-phosphonite can be obtained by treatment with an easily available dialkyl chlorophosphite, e.g., dimethyl chlorophosphite or diethyl chlorophosphite.

The reaction is preferably carried out in the presence of a solvent, and use can be made of a usual solvent which does not adversely influence the reaction. The aforementioned solvents can be used as preferred solvents. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The temperature at the dropwise addition of a chlorophosphite is from about −100° C. to about room temperature, and the addition is usually carried out under a cooled condition, for example, under cooling with dry ice-acetone bath or dry ice-2-propanol bath. The reaction temperature after the dropwise addition is from −100° C. to about reflux temperature of the solvent used, and usually, the reaction is preferably carried out at room temperature. If necessary, the compound (7) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of Step D is a reaction wherein the resulting phosphine-phosphonite is reduced to form a tertiary phosphine-primary phosphine. The reduction is achieved by treating the phosphine-phosphonite with a reagent which is known as a reducing agent in the field of organic synthesis, for example, a metal hydride such as lithium aluminum hydride. The amount of the reducing agent to be used ranges from 1 to 10 equivalents, preferably 2 to 8 equivalents relative to the phosphine-phosphonite.

The reaction is preferably carried out in the presence of a solvent, and use can be made of a usual solvent which does not adversely influence the reaction. Preferred is an inert solvent including an ether such as diethyl ether, diisopropyl ether, tetrahydrofuran (THF), 1,4-dioxane, or 1,2-dimethoxyethane, a hydrocarbon such as pentane, hexane, or methylcyclohexane, an aromatic hydrocarbon such as benzene, toluene, or chlorobenzene, or a halogenated hydrocarbon such as chloroform, dichloromethane, 1,2-dichloroethane, or carbon tetrachloride. These solvents may be used solely or as a mixed solvent. Moreover, the reaction can be suitably carried out in the presence of a Lewis acid such as trimethylsilyl chloride. Furthermore, the reaction can be suitably carried out under an inert gas atmosphere such as argon or nitrogen. The reaction temperature is from about −50° C. to about a reflux temperature of the solvent, and usually, the reaction is preferably carried out at a temperature of −30° C. to room temperature. If necessary, the compound (8) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of the first step of final Step E is a reaction of dimetalation of the resulting tertiary phosphine-primary phosphine by cleaving its P—H bond. The reagent for use in the metalation includes an alkali metal (e.g., lithium, sodium, or potassium), an alkaline earth metal (e.g., magnesium), or a derivative thereof (sodium-cyclopentadiene, sodium bistrimethylsilylamide, potassium hydride, potassium amide, or a Grignard reagent). Preferably, the dimetalation can be achieved by treating the compound with a reagent which is known as a lithiation reagent in the field of organic synthesis, such as methyllithium, n-butyllithium, sec-butyllithium, tert-butyllithium, phenyllithium, or lithium diiso-propylamide to cleave the P—H bond.

The reaction is preferably carried out in the presence of a solvent, and use can be made of a usual solvent which does not adversely influence the reaction. The aforementioned solvents can be used as preferred solvents. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The reaction temperature is from about −30° C. to about room temperature, and usually, the reaction is preferably carried out at a temperature of 0° C. to room temperature.

The reaction of the second step of final Step E is a reaction wherein the resulting bis(metal) compound is reacted with a bis(alkyl sulfonate) derivative of an optically active 1,4-diol to form an optically active phosphine-phosphorane which is a final product, the diol being producible by using the method described in a literature (Tetrahedron: Asymmetry 1991, 2, 569) and the derivative being obtainable by reacting the diol with a alkylsulfonyl chloride, preferably methanesulfonyl chloride in the presence of a tertiary amine such as triethylamine.

The reaction is preferably carried out in the presence of a solvent, and use can be made of a usual solvent which does not adversely influence the reaction. The aforementioned solvents can be used as preferred solvents. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The reaction temperature is from about −30° C. to about a reflux temperature of the solvent, and usually, the reaction is preferably carried out at a temperature of 0° C. to room temperature. If necessary, the resulting optically active phosphine-phosphorane compound (3) thus obtained can be isolated and purified by a known separation-purification procedure, for example, concentration, concentration under reduced pressure, solvent extraction, crystallization, recrystallization, or chromatography.

Various compounds of the formula (1) or (2) can be obtained using various 2-bromophenol derivatives instead of the above 2-bromophenol in Step A of the above production method, various di(substituted 1-naphthyl)phosphines instead of the above di(1-naphthyl)phosphine in Step B of the production method, and dimesylates of various optically active 1,4-diols (e.g., 3,6-octanediol, 4,7-decanediol, 3,6-dihydroxy-2,7-dimethyloctane, 1,4-dicyclohexyl-1,4-butanediol, and 1,4-di(trifluoromethyl)-1,4-butanediol) instead of the above dimesylate of optically active hexanediol in Step E of the production method.

Among the compounds of the invention, the compound (1), particularly an optically active compound (1) is useful as a ligand of a transition metal complex. Furthermore, the compound (2) is useful as a production intermediate of the compound (1).

The following will explain the transition metal complex. Preferred complexes include the following compounds.

A complex represented by the general formula (3):

$$M_mL_nX_pY_q \qquad (3)$$

(wherein M is a transition metal selected from the group consisting of Ir, Rh, Ru, Pd, and Ni and L represents the phosphine-phosphorane compound represented by the general formula (1) described in claim 1; and when M is Ir or Rh, X is Cl, Br, or I, and m=n=p=2 and q=0, when M is Ru, (i) X is Cl, Br, or I, Y represents a trialkylamino group, and m=n=2, p=4 and q=1, (ii) X is Cl, Br, or I, Y represents pyridyl group or a ring-substituted pyridyl group, and m=n=1, p=2, and q=2, (iii) X is a carboxylate group, and m=n=1, p=2 and q=0, or (iv) X is Cl, Br, or I, and m=n=p=2 and q=0, when M is Pd, (i) X is Cl, Br, or I, and m=n=1, p=2, and q=0 or (ii) X is an allyl group, and m=n=p=2 and q=0, and when M is Ni, X is Cl, Br, or I, and m=n=1, p=2, and q=0).

A complex represented by the general formula (4):

$$[M_mL_nX_pY_q]Z_s \qquad (4)$$

(wherein M is a transition metal selected from the group consisting of Ir, Rh, Ru, Pd, and Ni and L represents the phosphine-phosphorane compound represented by the general formula (1) described in claim 1; and when M is Ir or Rh, (i) X is 1,5-cyclooctadiene or norbornadiene, Z is $BF_4$, $ClO_4$, OTf, $PF_6$, $SbF_6$, or $BPh_4$, and m=n=p=s=1 and q=0 (ii) Z is $BF_4$, $ClO_4$, OTf, $PF_6$, $SbF_6$, or $BPh_4$, and m=s=1, n=2 and p=q=2 when M is Ru, (i) X is Cl, Br, or I, Y represents an aromatic compound or olefin compound which is a neutral ligand, Z is Cl, Br, I, $I_3$, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2, and when M is Pd or Ni, Z is $BF_4$, $ClO_4$, OTf, $PF_6$, $SbF_6$, or $BPh_4$, and m=n=1, p=q=0, and s=2, wherein Ph represents a phenyl group and Tf represents a triflate group ($SO_2CF_3$)).

A transition metal which forms the complex includes rhodium, ruthenium, iridium, palladium, nickel, and the like.

These transition metal complexes can be produced by a known method.

By the way, with regard to the symbols used in the formulae shown in the following transition metal complexes, L represents an optically active compound among the compounds (1) of the invention, cod represents 1,5-cyclooctadiene, nbd represents norbornadiene, Tf represents triflate group ($SO_2CF_3$), Ph represents phenyl group, Ac represents acetyl group, and Et represents ethyl group.

Rhodium Complex

As a specific example of producing a rhodium complex, the complex can be synthesized by reacting bis(cycloocta-1,5-diene) rhodium(I) tetrafluoroborate salt with Me-UCAP-(1-Nap) of the invention according to the method described in "4th edition Jikken Kagaku Koza (Lecture of Experimental Chemistry)", vol. 18, Organic Metal Complexes, 1991, Maruzen, pp. 339–344, edited by the Chemical Society of Japan. The following can be mentioned as specific examples of the rhodium complexes.

[Rh(L)Cl]$_2$, [Rh(L)Br]$_2$, [Rh(L)I]$_2$,
[Rh(cod)(L)]BF$_4$, [Rh(cod)(L)]ClO$_4$,
[Rh (cod)(L)]PF$_6$, [Rh(cod)(L)]BPh$_4$, [Rh(cod)(L)]OTf,
[Rh(nbd)(L)]BF$_4$, [Rh(nbd)(L)]ClO$_4$,
[Rh(nbd)(L)]PF$_6$, [Rh(nbd)(L)]BPh$_4$, [Rh(nbd)(L)]OTf,
[Rh(L)$_2$]BF$_4$, [Rh(L)$_2$]ClO$_4$,
[Rh(L)2]PF$_6$, [Rh(L)$_2$]BPh$_4$, [Rh(L)$_2$]OTf Ruthenium Complex As the method for producing a ruthenium complex, the complex can be prepared by heating [Ru(cod)Cl$_2$]$_n$ and Me-UCAP-(1-Nap) at reflux in toluene solvent in the presence of triethylamine as described in a literature (T. Ikariya, Y. Ishii, H. Kawano, T. Arai, M. Saburi, S. Yoshikawa, and S. Akutagawa, J. Chem. Soc., Chem. Commun., 1988, 922). Moreover, it can also be prepared by heating [Ru(p-cymene) I$_2$]$_2$ and Me-UCAP-(1-Nap) with stirring in methylene chloride and ethanol according to the method described in a literature (K. Mashima, K. Kusano, T. Ohta, R. Noyori, H. Takaya, J. Chem. Soc., Chem. Commun., 1989, 1208). The following can be mentioned as specific examples of the ruthenium complexes.

Ru(OAc)$_2$(L), Ru$_2$Cl$_4$(L)$_2$NEt$_3$,
[RuCl(benzene)(L)]Cl, [RuBr(benzene)(L)]Br,
[RuI(benzene)(L)]I,
[RuCl(p-cymene)(L)]Cl, [RuBr(p-cymene)(L)]Br, [RuI(p-cymene) (L)]I,
[Ru(L)](BF$_4$)$_2$, [Ru(L)](ClO$_4$)$_2$, [Ru(L)](PF$_6$)$_2$, [Ru(L)](BPh$_4$)$_2$,
[Ru(L)](OTf)$_2$ Iridium Complex The iridium complex can be prepared by reacting Me-UCAP-(1-Nap) with [Ir(cod)(CH$_3$CN)$_2$]BF$_4$ in tetrahydrofuran according to the method described in a literature (K. Mashima, T. Akutagawa, X. Zhang, T. Taketomi, H. Kumobayashi, S. Akutagawa, J. Organomet. Chem., 1992, 428, 213). The following can be mentioned as specific examples of the iridium complexes.

[Ir(L)Cl]$_2$, [Ir(L)Br]$_2$, [Ir(L)I]$_2$,
[Ir(cod)(L)]BF$_4$, [Ir(cod)(L)]ClO$_4$,
[Ir(cod)(L)]PF$_6$, [Ir(cod)(L)]BPh$_4$, [Ir(cod)(L)]OTf,
[Ir(nbd)(L)]BF$_4$, [Ir(nbd)(L)]ClO$_4$,
[Ir(nbd)(L)]PF$_6$, [Ir(nbd)(L)]BPh$_4$, [Ir(nbd)(L)]OTf,
[Ir(L)$_2$]BF$_4$, [Ir(L)$_2$]ClO$_4$, [Ir(L)$_2$]PF$_6$, [Ir(L)$_2$]BPh$_4$,
[Ir(L)$_2$]OTf Palladium Complex The palladium complex can be prepared by reacting Me-UCAP-(1-Nap) with π-allylpalladium chloride according to the method described in a literature (Y. Uozumi and T. Hayashi, J. Am. Chem. Soc., 1991, 113, 9887). The following can be mentioned as specific examples of the palladium complexes.

PdCl$_2$(L), (π-allyl)Pd(L), [Pd(L)]BF$_4$, [Pd(L)]ClO$_4$,
[Pd(L)]PF$_6$ , [Pd(L)]BPh$_4$, [Pd(L)]OTf Nickel Complex The nickel complex can be prepared by the method described in "4th edition Jikken Kagaku Koza (Lecture of Experimental Chemistry)", vol. 18, Organic Metal Complexes, 1991, Maruzene, p. 376, edited by the Chemical Society of Japan, or by dissolving Me-UCAP-(1-Nap) and nickel chloride in a mixed solvent of 2-propanol and methanol and heating them with stirring according to the method described in a literature (Y. Uozumi and T. Hayashi, J. Am. Chem. Soc., 113, 9887 (1991)). The following can be mentioned as specific examples of the nickel complexes.

NiCl$_2$(L), NiBr$_2$(L), NiI$_2$(L)

The transition metal complex containing the novel optically active phosphine-phosphorane compound as a ligand is useful as a catalyst for asymmetric hydrogenation. In the case of using the complex as the catalyst, the complex may be used after increasing its purity or the complex may be used without purification.

Among the above transition metal complexes, complexes containing rhodium and an optically active phosphine-phosphorane compound, 1-((2S,5S)-2,5-dimethylphosphorano)-2-[di(1-naphthyl)phosphino]benzene (3) (hereinafter, sometimes referred to as (S,S)-Me-UCAP-(1-Nap)) as a ligand can achieve a higher enantioselectivity and a higher catalytic activity as compared with rhodium complexes containing BINAP, Me-DuPHOS, or the like as a ligand in the asymmetric hydrogenation of N-benzoyl-l-phenylpropenamine.

The novel diphosphine compound of the invention is particularly useful as a ligand for a transition metal complex. Moreover, the transition metal complex is useful as a catalyst for asymmetric hydrogenation, and also is industrially extremely useful.

The following will explain the invention in detail with reference to Examples and Use Examples, but the invention is by no means limited thereto.

By the way, the instruments employed for measuring physical properties in each Example are as follows.

Nuclear magnetic resonance
DRX500 (BRUKER JAPAN CO. LTD.)

| | |
|---|---|
| $^1$H NMR | 500.13 MHz |
| $^{31}$P NMR | 202.46 MHz |
| Melting point | Yanaco MP-500D |
| Optical rotation | Nihon Bunko, DIP-4 |
| Gas chromatography | GLC Hewlett Packard 5890-II |
| High performance liquid chromatography | HPLC Shimadzu Corp. LC10AT & SPD10A |
| Mass spectrometry | MASS Hitachi Ltd. M-80B |

EXAMPLE 1

Synthesis of 1-((2S,5S)-2,5-dimethylphosphorano)-2-[di(1-naphthyl)phosphino]benzene (hereinafter, referred to as (S,S)-Me-UCAP-(1-Nap))

(a) Synthesis of 2-(trifluoromethanesulfonyl)oxybromobenzene (5)

Into a four-neck flask was weighed 250.00 g (1.445 mol) of 2-bromophenol, and the atmosphere of the reaction vessel fitted with a thermometer, a condenser tube, and a dropping funnel with a pressure-equalizing tube was completely replaced with nitrogen. Thereto were added 1,500 mL of anhydrous methylene chloride and 171.40 g (2.168 mol) of pyridine, followed by cooling to 0° C. After the dropwise addition of 448.45 g (1.590 mol) of trifluoromethanesulfonic anhydride over a period of 2 hours, the whole was stirred at room temperature for 2 hours. The resulting mixed solution was poured into 500 mL of 2N hydrochloric acid aqueous solution, the mixture was stirred at room temperature for 30 minutes, and then the layers were separated from each other. The resulting organic layer was washed with water and saturated saline and dried over anhydrous magnesium, and then the solvent was removed by evaporation under reduced pressure. The residue was purified by distillation under reduced pressure to obtain the title compound (425.32 g, a colorless oily substance). Yield 96.5%.

bp: 112–113° C./1995–2128Pa $^1$H NMR (CDCl$_3$): δ; 7.2–7.4 (m, 3H), 7.6–7.8 (m, 1H)

(b) Synthesis of (2-bromophenyl)[di(1-naphthyl)]phosphine (6)

Into a four-neck flask were weighed 16.89 g (59.0 mmol) of di(1-naphthyl)phosphine, 1.27 g (2.5 mmol) of Pd$_2$(dba)$_3$CHCl$_3$ (dba represents dibenzylideneacetone), and 1.01 g (2.5 mmol) of diphenylphosphinopropane. The atmosphere of the reaction vessel fitted with a thermometer, a condenser tube, and a dropping funnel with a pressure-equalizing tube was completely replaced with nitrogen. Thereto were added 150 mL of toluene, 15.00 g (49.2 mmol) of 2-(trifluoromethanesulfonyl)oxy-bromobenzene (5), and 9.53 g (73.8 mmol) of diisopropylethylamine, followed by 16 hours of heating at reflux. After the completion of the reaction, the reaction mixture was cooled to room temperature and poured into 150 mL of 5% hydrochloric acid aqueous solution. After 30 minutes of stirring, the layers were separated from each other. The organic layer was washed with water and saturated saline and dried over anhydrous magnesium sulfate. Toluene was removed by evaporation and the residue was purified by silica gel column chromatography to obtain the title compound (10.68 g, a pale yellow solid). Yield 49.2%.

mp: 206–207° C.

$^1$H NMR (CDCl$_3$): δ; 6.70 (dt, J=2.2, 7.7 Hz, 1H), 6.98 (t, J=5.5 Hz, 2H), 7.09 (dt, J=1.1, 7.4 Hz, 1H), 7.20 (dt, J=1.9, 7.6 Hz, 1H), 7.32 (t, J=7.8 Hz, 2H), 7.44–7.47 (m, 2H), 7.50 (dt, J=1.1, 7.4 Hz, 1H), 7.66 (ddd, J=1.1, 3.9, 8.2 Hz, 1H), 7.89 (t, J=8.8 Hz, 4H), 8.49 (dd, J=4.8, 8.2 Hz, 2H)

$^{31}$P NMR (CDCl$_3$): δ; –20.7 (s)

EI-MS (m/z): 440 ([M–1]$^+$)

(c) Synthesis of diethyl 2-[di(1-naphthyl)phosphino]phenylphosphonite (7)

Into a four-neck flask was weighed 10.00 g (22.7 mmol) of (2-bromophenyl)[di(1-naphthyl)]phosphine (6). The atmosphere of the reaction vessel fitted with a thermometer, a condenser tube, and a dropping funnel with a pressure-equalizing tube was completely replaced with nitrogen, and 100 mL of anhydrous tetrahydrofuran (hereinafter referred to as THF) was added thereto. Thereto was added dropwise 14.8 mL (23.8 mmol) of n-butyllithium-hexane (1.6 M) solution at –78° C. over a period of 30 minutes, followed by 1 hour of stirring at the same temperature. The resulting mixed solution was cooled to –78° C. and thereto was added dropwise a 10 mL THF solution of 3.92 g (23.8 mmol) of diethyl chlorophosphite (manufactured by Aldrich) over a period of 30 minutes. After the dropwise addition, a cooling bath was removed and the whole was further stirred at room temperature for 15 hours. After the completion of the reaction, THF was removed by evaporation, the residue was dissolved in 50 mL of diethyl ether, and insoluble matter was removed by filtration. The solvent was removed by evaporation and the residue was purified by active alumina column chromatography (eluent: hexane/ethyl acetate=4/1) to obtain the title compound (8.83 g, a pale yellow solid). Yield 81.0%.

mp: 94–95° C.

$^{31}$P NMR (CD$_2$Cl$_2$): δ; 153.2. (d, J$_{p\text{-}p}$=156 Hz), –32.7 (d, J$_{p\text{-}p}$=156 Hz)

EI-MS (m/Z): 482 ([M]$^+$)

(d) Synthesis of 2-[di(1-naphthyl)phosphino]phenylphosphine (8)

Under a nitrogen atmosphere, 5.74 g (52.9 mmol) of trimethylsilyl chloride was added dropwise to a 75 mL THF suspension of 2.01 g (52.9 mmol) of lithium aluminum hydride at –30° C. over a period of 30 minutes, and after the dropwise addition, the whole was stirred at room temperature for 1.5 hours. Then, a 50 mL THF solution of 8.50 g (17.6 mmol) of diethyl 2-[di(1-naphthyl)phosphino]phenylphosphonite (7) was added dropwise at –30° C. over a period of 30 minutes and the whole was stirred at room temperature for 16 hours. Thereto was gradually added dropwise a 15 mL THF solution of 7.5 mL of water at 0° C. to 10° C., and then 30 mL of 1N sodium hydroxide aqueous solution was added. Under a nitrogen atmosphere, the organic layer was decanted and the solvent was removed by evaporation. The residue was dissolved in 30 mL of diethyl ether, and the solution was washed three times with 10 mL of water degassed beforehand and then, dried over anhydrous sodium sulfate. The drying agent was removed and the solvent was removed by evaporation to obtain the title compound (6.50 g, a white viscous solid). Yield 93.5%.

mp: 49–50° C.

$^{31}$P NMR (CDCl$_3$): δ; –27.9 (d, J$_{p\text{-}p}$=102 Hz), –124.4 (d, J$_{p\text{-}p}$=102 Hz)

EI-MS (m/Z): 394 ([M]$^+$)

(e) Synthesis of 1-((2S,5S)-2,5-dimethylphosphorano)-2-[di(1-naphthyl)phosphino]benzene (3) (hereinafter referred to as (S,S)-Me-UCAP-(1-Nap))

Under a nitrogen atmosphere, 1.00 g (2.5 mmol) of 2-[di(1-naphthyl)phosphino]phenylphosphine (8) was dissolved into 30 mL of THF, and 3.3 mL (5.3 mmol) of n-butyllithium-hexane (1.6 M) solution was added dropwise at 0° C. over a period of 30 minutes, followed by 1 hour of stirring at the same temperature. Then, a 5 mL THF solution of 0.73 g (2.7 mmol) of (2R,5R)-2,5-hexanediol bis(methanesulfonate) obtainable by the method described in a literature (M. J. Burk, J. E. Feaster and R. L. Harlow, Tetrahedron: Asymmetry, 1991, 2, 569) and the like was added dropwise thereto at 0° C. over a period of 30 minutes. After the dropwise addition, the whole was stirred at 0° C. for 1 hour and then at room temperature for 16 hours. Thereafter, 1 mL of methanol was added at room temperature and the solvent was removed by evaporation. The resulting residue was purified by active alumina column chromatography (eluent: hexane/methylene chloride=2/1) to obtain the title compound (0.29 g, a white solid). Yield 24.0%.

mp: 245–246° C.

[α]$_D^{25}$+226.0° (c=1.10, CH$_2$Cl$_2$)

$^1$H NMR (CDCl$_3$):δ; 0.95–1.06 (m, 6H), 1.25–1.35 (m, 1H), 1.60–1.69 (m, 1H), 2.00–2.08 (m, 1H), 2.17–2.26 (m, 1H), 2.27–2.40 (m, 1H), 2.57–2.66 (m, 1H), 6.75–6.78 (m, 1H), 6.92–6.96 (m, 2H), 7.08–7.11 (m, 1H), 7.25 (t, J=7.6 Hz, 1H), 7.30–7.35 (m, 2H), 7.38–7.52 (m, 4H), 7.61–7.64 (m, 1H), 7.84 (t, J=7.2 Hz, 2H), 7.89 (dd, J=4.4, 7.7 Hz, 2H), 8.39 (dd, J=4.7, 8.5 Hz, 1H), 8.50–8.52 (m, 1H)

$^{31}$P NMR (CDCl$_3$): δ; 0.4 (d, J$_{p\text{-}p}$=164 Hz), –28.0 (d, J$_{p\text{-}p}$=164 Hz)

EI-MS (m/Z): 475 ([M–1]$^+$)

EXAMPLE 2

Synthesis of [Rh(cod)((S,S)-Me-UCAP-(1-Nap))]OTf

Under a nitrogen atmosphere, 68.8 mg (0.147 mmol) of [Rh(cod)$_2$]OTf was dissolved into 3 mL of methylene chloride in a 20 mL Schlenk tube, and then a 5 mL methylene chloride solution of 70.0 mg (0.147 mmol) of (S,S)-Me-UCAP-(1-Nap) (3) was added thereto at room temperature. After 1 hour of stirring at the same temperature, the solvent was removed by evaporation. The residue was recrystallized from methylene chloride-diethyl ether to obtain the title compound (117 mg, golden yellow crystals). Yield 95.0%.

$^{31}$P NMR (CD$_2$Cl$_2$) δ; 75.9 (dd, J=23, 146 Hz), 47.7 (dd, J=23, 146 Hz)

EXAMPLE 3

Comparative Examples 1 and 2

Asymmetric hydrogenation of N-benzoyl-1-phenylpropenamine

Under a nitrogen atmosphere, 0.0018 mmol of [Rh(cod)(L)]OTf, 213.6 mg (0.9 mmol) of N-benzoyl-1-phenylpropenamine, and 3 mL of methanol were placed in a stainless steel autoclave, followed by 15 hours of stirring at 30° C. under a hydrogen pressure of 0.4 MPa. The reaction mixture was subjected to GLC and HPLC analysis to measure conversion, optical purity, and absolute configuration. The results obtained are shown in Table 1.

<GLC analytical conditions>
Conversion was measured using a capillary column HP-1 (manufactured by Hewlett Packard).

<HPLC analytical conditions>
Enantioselectivity was measured using CHIRALCEL OD (4.6×250 mm, manufactured by Daicel Chemical Industries, Ltd.).

TABLE 1

Asymmetric hydrogenation of N-benzoyl-1-phenylpropenamine

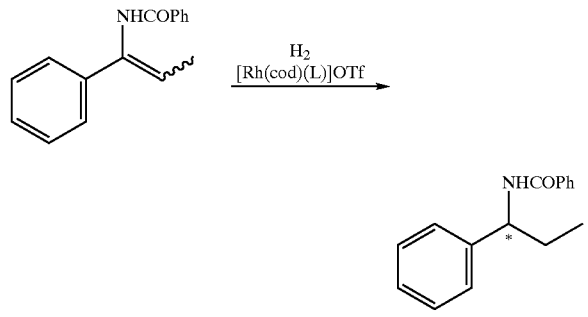

| Reaction Example | L | Conversion (%) | Enantio-selectivity (% ee) | Absolute configuration |
|---|---|---|---|---|
| Example 3 | (S,S)-Me-UCAP-(1-Nap) | 56.2 | 98.9 | S |
| Comparative Example 1 | (R)-BINAP | 6.6 | 34.6 | S |
| Comparative Example 2 | (R,R)-Me-DuPHOS | 25.4 | 77.6 | R |

While the invention has been described in detail and with reference to specific embodiments thereof, it will be apparent to one skilled in the art that various changes and modifications can be made therein without departing from the scope thereof.

This application is based on Japanese patent application No. 2001-375218 filed Dec. 10, 2001, the entire contents thereof being hereby incorporated by reference.

What is claimed is:

1. A phosphine-phosphorane compound represented by the formula (1):

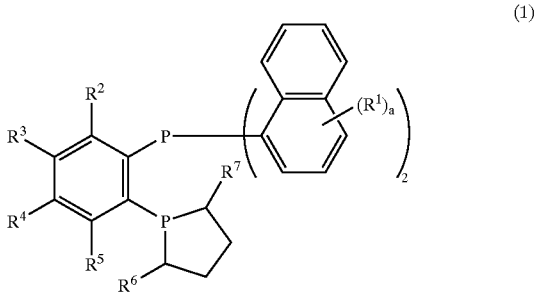

(1)

wherein $R^1$ represents hydrogen atom, a linear or branched alkyl group having 1 to 4 carbon atoms, or an alkoxy group having 1 to 6 carbon atoms and a represents an integer of 1 to 4; $R^2$, $R^3$, $R^4$, and $R^5$ are the same or different, and each represents hydrogen atom, an alkyl group having 1 to 6 carbon atoms, or an alkoxy group having 1 to 6 carbon atoms, and each of $R^2$ and $R^3$, $R^3$ and $R^4$, and $R^4$ and $R^5$ may be together combined to form a ring which may contain one or more oxygen atoms; and $R^6$ and $R^7$ are the same or different, and each represents a linear or branched alkyl group having 1 to 6 carbon atoms, a cycloalkyl group having 3 to 7 carbon atoms, a perfluoroalkyl group, a phenyl group, a phenyl group having one or more substituents each selected from the group consisting of an alkyl group having 1 to 6 carbon atoms, an alkyl group having 1 to 6 carbon atoms which is substituted by one or more halogen atoms, an alkoxy group having 1 to 6 carbon atoms, and a halogen atom, an aralkyl group having 7 to 12 carbon atoms, or a ring-substituted aralkyl group.

2. A tertiary phosphine-primary phosphine compound represented by the formula (2):

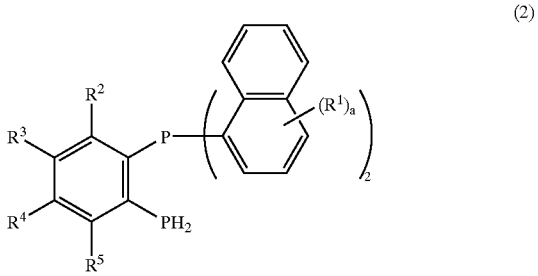

(2)

wherein $R^1$ represents hydrogen atom, a linear or branched alkyl group having 1 to 4 carbon atoms, or an alkoxy group having 1 to 6 carbon atoms and a represents an integer of 1 to 4; and $R^2$, $R^3$, $R^4$, and $R^5$ are the same or different, and each represents hydrogen atom, an alkyl group having 1 to 6 carbon atoms, or an alkoxy group having 1 to 6 carbon atoms, and each of $R^2$ and $R^3$, $R^3$ and $R^4$, and $R^4$ and $R^5$ may be together combined to form a ring which may contain one or more oxygen atoms.

3. A transition metal complex comprising the phosphine-phosphorane compound represented by the formula (1) according to claim 1 and a transition metal, wherein the transition metal is selected from the group consisting of Ir, Rh, Ru, Pd, and Ni.

4. A catalyst for asymmetric synthetic reactions, which comprises the transition metal complex according to claim 3.

5. The catalyst for asymmetric synthetic reactions according to claim 4, wherein the transition metal complex is represented by the formula (3):

$$M_mL_nX_pY_q \qquad (3)$$

(wherein M is a transition metal selected from the group consisting of Ir, Rh, Ru, Pd, and Ni and L represents the phosphine-phosphorane compound represented by the general formula (1) according to claim 1; and when M is Ir or Rh, X is Cl, Br, or I, and m=n=p=2 and q=0, when M is Ru, (i) X is Cl, Br, or I, Y represents a trialkylamino group, and m=n=2, p=4 and q=1, (ii) X is Cl, Br, or I, Y represents pyridyl group or a ring-substituted pyridyl group, and m=n=1, p=2, and q=2, (iii) X is a carboxylate group, and m=n=1, p=2 and q=0, or (iv) X is Cl, Br, or I, and m=n=p=2 and q=0, when M is Pd, (i) X is Cl, Br, or I, and m=n=1, p=2, and q=0 or (ii) X is an allyl group, and m=n=p=2 and q=0, and when M is Ni, X is Cl, Br, or I, and m=n=1, p=2, and q=0).

6. The catalyst for asymmetric synthetic reaction according to claim 4, wherein the transition metal complex is represented by the formula (4):

$$[M_mL_nX_pY_q]Z_s \qquad (4)$$

(wherein M is a transition metal selected from the group consisting of Ir, Rh, Ru, Pd, and Ni and L represents the phosphine-phosphorane compound represented by the general formula (1) according to claim 1; and when M is Ir or Rh, (i) X is 1,5-cyclooctadiene or norbornadiene, Z is $BF_4$, $ClO_4$, OTf, $PF_6$, $SbF_6$, or $BPh_4$, and m=n=p=s=1 and q=0 or (ii) Z is $BF_4$, $ClO_4$, OTf, $PF_6$, $SbF_6$, or $BPh_4$, and m=s=1 p=n=2 and p=q=0, when M is Ru, (i) X is Cl, Br, or I, Y represents an aromatic compound or olefin compound which is a neutral ligand, Z is Cl, Br, I, $I_3$, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2, and when M is Pd or Ni, Z is $BF_4$, $ClO_4$, OTf, $PF_6$, $SbF_6$, or $BPh_4$, and m=n=1, p=q=0, and s=2, where Ph represents a phenyl group and Tf represents a triflate group ($SO_2CF_3$)).

7. A catalyst for asymmetric hydrogenation, which comprises the transition metal complex according to claim 3.

* * * * *